US005299253A

United States Patent [19]

Wessels

[11] Patent Number: 5,299,253
[45] Date of Patent: Mar. 29, 1994

[54] ALIGNMENT SYSTEM TO OVERLAY ABDOMINAL COMPUTER AIDED TOMOGRAPHY AND MAGNETIC RESONANCE ANATOMY WITH SINGLE PHOTON EMISSION TOMOGRAPHY

[75] Inventor: Barry W. Wessels, Centerville, Va.
[73] Assignee: Akzo N.V., Arnhem, Netherlands
[21] Appl. No.: 866,060
[22] Filed: Apr. 10, 1992
[51] Int. Cl.$^5$ .............................................. H05G 1/28
[52] U.S. Cl. ........................................ 378/163; 378/20
[58] Field of Search ................. 378/162, 163, 164, 20

[56] References Cited

U.S. PATENT DOCUMENTS 4,884,566 12/1989 Mounty .............................. 378/205
4,971,060 11/1990 Schmuder et al. ................. 378/163

OTHER PUBLICATIONS

Pelizzari, C. A. et al., "Accurate Three-Dimensional Registration of CT, PET, and/or MR Images of the Brain", *J. of Computer Assisted Tomography*, vol. 13, No. 1, 1989, pp. 20-26.

Wallis, J. W. et al., "Three-Dimensional Display in Nuclear Medicine and Radiology", *J. of Nuclear Medicine*, vol. 32, No. 3, Mar. 1991, pp. 534-546.

Kramer, E. L. et al., "CT-SPECT Fusion for Analysis of Radiolabeled Antibodies: Applications in Gastrointesinal and Lung Carcinoma", *Nucl. Med. Biol.*, vol. 18, No. 1, 1991, pp. 27-42.

*Primary Examiner*—Craig E. Church
*Attorney, Agent, or Firm*—Spencer, Frank & Schneider

[57] ABSTRACT

The invention is a machine based alignment system for imaging with a contrasting marker (fiducial marker) attached to a support means for providing a set of markings which uniquely identify each cross-section of an imaged object in relation to other registered images.

The invention also provides a method for using the alignment system.

17 Claims, 1 Drawing Sheet

ALIGNMENT SYSTEM TO OVERLAY ABDOMINAL COMPUTER AIDED TOMOGRAPHY AND MAGNETIC RESONANCE ANATOMY WITH SINGLE PHOTON EMISSION TOMOGRAPHY

BACKGROUND OF THE INVENTION

1. Field of the Invention

The present invention relates to an alignment system used for overlaying or registering uptake patterns displayed by Single Emission Photon Tomography with specific underlying anatomy by Computer Aided Tomography and/or Magnetic Resonance. The alignment system creates a set of markings in each image which uniquely identifies a cross-section of the imaged object. The invention also relates to a method of using the alignment system.

2. Description of the Related Art

High specificity and the ability to detect occult tumors has made monoclonal antibodies (Mabs) useful as vehicles for targeting diaonostic doses of radionuclides to tumors (Goldenberg et. al., 3 Antibody Immunoconjugates and Radiopharmaceuticals, 151–167 (1990)). Recently, it has been shown that the highest accuracy rates are found for Mabs labeled with I-131, I-123, or Tc-99m (Goldenberg et. al., 3 Antibody Immunoconjugates and Radiopharmaceuticals, 151–167 (1990)). The use of single photon emission tomography (SPECT) for antibody imaging has compelled the investigator to correlate findings of SPECT with computed tomography (CT) and magnetic resonance (MR) images, because although CT and MR images are more accurate than SPECT images they suffer from a lack of physiological information. Correlation of the images is especially useful to identify lesions near the organs, such as liver, kidney, spleen, bladder and major blood vessels where the tumor activity uptake may be shadowed by the uptake of the adjacent organ. Different image registration methods were developed to perform image correlation. A surface fitting method has been described to register head scans (Chen et. al., Important Adv. Oncol., 131–134 (1990). It has the advantage that no specific headholders or positioning need be performed during data acquisition but it requires an expert for identification of regions of interest (ROI) and is not suitable for Mab images, because of the lack of anatomical landmarks. This technique also requires a rigid structure which the skull and to some extent the features of the brain provide more than the abdomen or the torso. Other disadvantages include 1) identified organ used as fiducial is sufficient only for "local" region; 2) requires time consuming contouring; 3) not being a general method, therefore anatomical markers have to be uniquely identified each time; and 4) organ dependence-non-tumor concentration of radiolabel uptake is variable.

Another method has been described to register gastrointestinal and lung carcinoma images (Kramer et. al., 172 Radiology, 861–865 (1989)) and Kramer et. al., 1 Nucl. Med. Bio., 27–42 (1991)). That method uses external and anatomical land- marks. Each landmark from the reference image is cross-correlated with the corresponding landmark from the other image. The differences between the two images are compensated through the warping algorithm which allows for translation, rotation, scale, and skew. Although registered images are accurate this method suffers from the disadvantages which are 1) repeated precise application of external markers and frame is difficult on a "moving" patient; 2) matching a external marker with an anatomical landmark may be problematic; 3) choosing the same pair of points from two images is operator and "movement" dependent; and 4) since only one cross-section is matched from each study, if there is a translation or rotation which is different in another cross-section, they may accumulate interpolation error.

There is thus a need for image alignment system which is machine based and uses external landmarks. In particular, there is a need for an alignment system which is 1) free from motion artifact; 2) organ independent, so concentration of radiolabel uptake in the organs is not a factor; 3) allows for minimum operator interference; 4) can be generally used for every patient; 5) where rotation and translation of the patient is not a problem; and 6) where the alignment system is machine compatible with minimal additional effort needed from the machine operator.

SUMMARY OF THE INVENTION

The present invention provides an alignment system for imaging comprising:

(A) a support means; and (B) a contrasting marker means attached to said support means, for providing a set of markings which uniquely identifies a cross-section of an imaged object.

The invention also provides a method for using the alignment system.

BRIEF DESCRIPTION OF THE DRAWINGS

The foregoing objects and advantages of the present invention, together with other advantages which may be attained by the principles of the present invention, will become more apparent upon reading the following detailed description of the invention in conjunction with the drawings.

The Figure shows an example of an alignment system, and (b) shows given the cross-sectional cuts taken in (a) the schematic of the unique set of markings at each cross-section.

DETAILED DESCRIPTION OF THE INVENTION

Figure 1B:
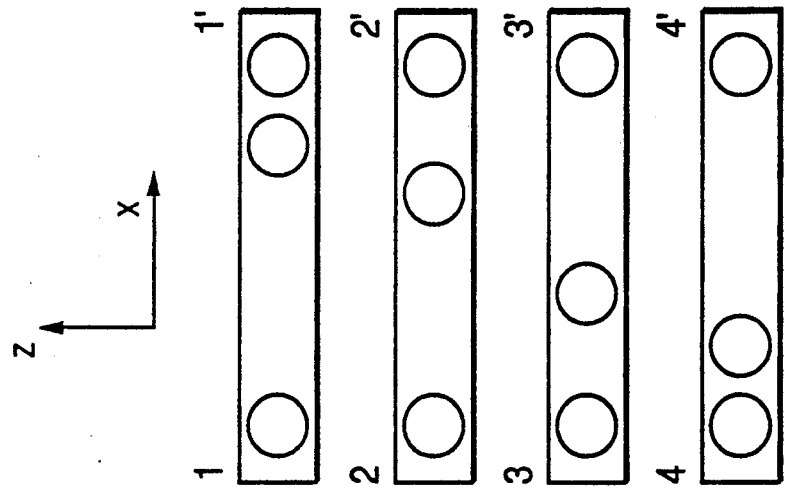

The present invention is based upon the need for an alignment system to provide a process for overlaying or registering uptake patterns displayed by single photon emission tomography with specific underlying anatomy by computer tomography and/or magnetic resonance. By incorporation of this alignment system into the imaging process this will allow for placement of regions of interest (ROI) on magnetic resonance or computer tomography images that correspond dimensionally to single photon emission tomography images from the same object.

The invention provides an alignment system for imaging comprising:

(A) a support means; and (B) a contrasting marker means attached to said support means, for providing a set of markings which uniquely identifies a cross-section of an imaged object. The imaged object is preferably a human torso, e.g. pelvis, abdomen and thorax.

The support means (A) may be a suspension system. The suspension system may be such known methods of suspension including wires, metal frames, or any other means for suspension as known in the art. The alignment system is machine based, rather than body based like some of the past systems.

More preferably, the support means (A) may be a material encasement. The term "material encasement" herein is meant to be an encapsulation of the contrasting marker(s) in a inert material. The term "inert" herein is meant to mean that which is not distinguishable to or does not interfere with the images obtained with the imaging system being used.

The material used for the material encasement may be a polymer, a wood, a foam, a metal, a ceramic or any combination of these materials as long as the material being used is inert to the imaging system being used. More preferably the material being used would be a wood, a foam or a polymer.

The "contrasting marker" (B) herein is meant to be a marker whose outline can accurately be viewed without distortion or blurring with the imaging system being used. The contrasting marker (B) can be many shapes including that of a solid or a hollow tube, or any other shape which one skilled in the art might utilize. The cross-section of the marker can have various shapes also including circular, square or any other cross-sectional shape of the marker that one skilled in the art might utilize.

The most preferable embodiment of the invention would utilize a circular cross-section with a diameter from about 0.5 mm to about 1.0 mm. Circular cross-section shape is selected for the contrasting marker because it was shown to have the best performance compared to the diamond and square cross-section shaped contrasting markers. It is important to note that a contrasting marker with a cross-section which is too large might potentially interfere with the images by blocking or distorting parts of the image, while a contrasting marker cross-section, which is too small might not be perceived in the image.

The "contrasting agent" herein is meant to be a solid, liquid, or gas which is readily discernable with the particular type of imaging used. For a contrasting marker (B) in the shape of a hollow tube, the contrasting agent would be any chemical composition which can fill said tube and is sufficiently contrasting with the particular imaging system used.

Contrasting agents generally used are iodine based contrast solution for radiographic scanning with computer tomography; $MnCl_2$ for magnetic resonance; and Tc99m for single photon emission tomography. Other contrasting agents commonly used include 111-IN, 131-I or 186-Re, however, this list is not exhaustive and should be thought to include other contrasting agents used by those skilled in the art.

Referring now to the Figure, the pattern of the contrast marker(s) provides for a set of markings which uniquely identifies the cross-section of the imaged object. For example, the four lines 1-1', 2-2', 3-3', and 4-4' which dissect the Figure can be thought to create four cross-sections of the Figure. The Figure for convention can be held to be in the x-y plane as is labeled on the Figure. The Figure attempts to present a schematic of what these cross-sections would look like in the x-z plane. In each of the schematics, the contrast markers would provide a set of markings which uniquely identify the cross-section. In one embodiment by keeping one of the contrasting markers or a series of contrasting markers constant along a longitudinal axis of the object being imaged, the operator can be assured of not looking at the mirror image of the object being imaged. The purpose of changing at least one contrast marker is to provide a constantly changing reference with respect to the contrast marker which remains constant along the transverse axis. Because this provides a unique set of markings, the operator can reference images from two different types of scans together by just matching the reference markings. Because of the combination of at least one transversely constant-longitudinally variable contrast marker and at least one transversely variable-longitudinally constant contrast marker, the operator also has the ability to quickly determine based on scaling where the cross-section was taken along the longitudinal axis of the alignment system. The operator can align the images from two or more imaging systems by hand or by computer with specially written computer programs.

Figure 1A:
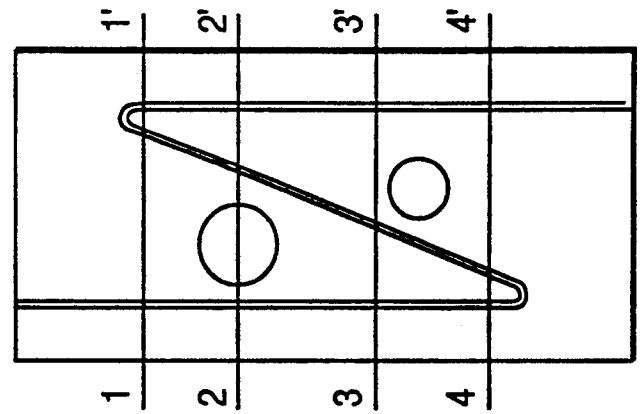

The pattern of the contrast markers is not limited to any particular pattern, however the pattern must be such that there is at least one transversely constant contrast marker and at least one transversely variable contrast marker spanning the longitudinal imaging area. The preferred pattern of the contrast markers is in the shape of an N such as in FIG. 1. However, depending on the direction of imaging, the images sought to be taken, the orientation of the object to be imaged and other factors known to those skilled in the art, examples of these contrast markers can be in the form of the letters Z, W with straight edges or M with straight edges pattern and allow for alignment by the above mentioned process. The shapes listed above are not all inclusive and any shape which would be apparent to someone skilled in the art is considered as part of this invention. It has been found that the greater the number of contrast marker reference points along a cross-section, the greater the accuracy and ease of alignment.

Another embodiment of this invention employs only transversely variable reference markers. The major difference with this and the previous embodiment is that with a transversely constant contrast marker is that the transversely constant contrast marker adds one more degree of orientation. An example of these contrast marker patterns is a contrast marker patterns in the shape of a letter V. This shape is not all inclusive and any shape which would be apparent to one skilled in the art is considered as part of the embodiment of this invention.

Although in the previous two embodiments the alignment system is used just in one plane, there can be a series of alignment systems in planes about the object to be imaged which would add to the accuracy of matching the images.

Another embodiment of the invention is a method of registering single photon emission tomography images with computer tomography or magnetic resonance images comprising the steps:

(A) supporting an object to be imaged on a support means;

(B) placing at least a portion of said object to be imaged adjacent to a contrasting marker means attached to said support means, (C) imaging object using two or more imaging techniques to produce at least two images of said object to be imaged, and (D) registering said at least two images of said object to be imaged to produce a coherent image of said object to be imaged.

More preferably, the supporting means (A) is a partial cast of the object's external shape. This can be accomplished by placing the object on a bag filled with a castable foam, and the cast can be formed to the desired contour.

The placing at least a portion of said object to be imaged adjacent to the marker (B). Examples of this include casting the contrasting marker alignment system in the bag filled with castable foam; placing the contrasting marker encapsulated in materials underneath the cast of the objects contour, but aligned with both the cast and the imaging machine; or suspending the contrasting marker alignment system above the object to be imaged. The alignment system is therefore strictly machine based and not body based like previous methods.

The imaging the object using two or more imaging techniques to produce at least two images of said object to be imaged (C). Examples of this include imaging by single photon emission tomography, computer tomography, or magnetic resonance.

Registering said at least two images of said object to be imaged to produce a coherent image of said object to be imaged (D). Examples of this include manual or computer aided registration using the alignment contrast markings.

EXAMPLES

In order that persons in the art may better understand the practice of the present invention, the following Examples are provided by way of illustration, and not by way of limitation. Additional background information known in the art may be found in the references cited herein, which are hereby incorporated by reference.

EXAMPLE 1

An alignment system was created with an contrasting marker in the shape of the letter N. The marker was then embedded into a wood board as the material encasement. The wood board had the dimensions of 38 cm×61 cm. Two holes were cut from the wood board of different diameters to assist with alignment of the machine based system. The width of the contrasting marker of the shape of the letter N between the two straight edges was 17 cm. The contrasting marker was made from a rubber tube with a 6 mm outer(4 mm inner) diameter, bent on both sides in the shape of the letter N. The contrasting marker had a port for filling with contrasting agent. The contrasting marker was filled with iodine based contrasting solution for computer tomography, MnC12 for magnetic resonance and Tc-99m for single photon emission tomography.

EXAMPLE 2

An alignment system is created with a contrasting marker in the shape of the letter W with straight edges. A patient specific cast is prepared. Alpha Cradle Brand AC 250 foaming agent (Smithers Medical Products Inc.) is used as a casting material. Following manufacturer's instructions the two solutions are mixed, and placed into a specially provided bag. Prior to placing the solutions in the bag, a contrasting marker in the form of the letter W with straight edges is placed in the plastic bag. The contrasting marker should be built to fit over an area with the width dimension being from about 10 cm min/ to about 50 cm max and the length being from about 20 cm min/ to about 250 cm max. A port opening to the contrasting marker is left outside the cast for filling the contrasting marker with contrasting agent. Upon filling the bag with a solution as mentioned earlier, the patient is placed on the bag which can be formed to the contour of the patient as desired. The contrasting marker is then filled with an iodine based contrasting solution for computer tomography, $MnCl_2$ for magnetic resonance and Tc-99m for single photon emission tomography.

EXAMPLE 3

Body Cast

Before any type of imaging study, a patient specific cast was prepared. Alpha Cradle Brand AC 250 foaming agent (Smithers Medical Products Inc.) was used as a casting material. Following the manufacturer's instructions two solutions are mixed, and placed into a specially provided bag. The patient was placed on the bag which was formed to contour the patient. After approximately 6 minutes the cast had hardened and conformed to the patient's body shape. Although the patient can lie comfortably in the cast, the cast covers the patient tightly and greatly reduces motion artifact. An N-shaped contrasting marker, encased into a wood board, was placed under the cast. It was a rubber tube with 6 mm outer (4 mm inner) diameter, bent on both sides. Circular cross-section shape is selected for the contrasting marker (rubber tube) because it had shown the best performance among the diamond and square cross-section shaped contrasting markers (Bose et. al., Radiology, 1197–1200 (1989)). The contrasting marker was filled with contrasting agent with an iodine based contrasting solution to be used with computer tomography, $MnCl_2$ for magnetic resonance imaging and Tc99m for single photon emission tomography studies. The cast was secured to the wood board which contained the marker system. Also the board is secured to the imaging table to avoid translational movements during the scan. Although table curvatures are different for imaging machines the board provided equal distance between the contrasting markers and the patient for different scan tables.

Data Acquisition and Analysis

An Oldelft SMX simulator was used to take anterior-posterior, posterior-anterior X-ray films to demonstrate the correct alignment of the contrasting marker alignment system, the body cast and the patient. After fabrication of the body cast, the simulator was used to put crossmarks for the pelvic and hepatic areas on the cast. These crossmarks are used to set the patient to the center of the imaging machine. Since the patient uniquely fits into the cast, it is an easy task to ensure the reproducibility of setting the patient into the imaging machine in each imaging session.

Functional (SPECT) and anatomical (CT or MR) data sets are used for image registration purpose. The study has made use of transaxial slices, but wherever necessary, sagittal and coronal reconstruction has been performed. Transaxial CT images were acquired using CT 9800 system(General Electric Co., Milwaukee, Wis.). Transaxial and sagittal MR images obtained using a 1.5 Tesla Signa system (General Electric Co., Milwaukee, Wis.). For SPECT studies Prism 30000S (Picker International Inc., Bedford Heights, Ohio) 3 headed SPECT camera with low and medium energy collimator was used. The imaging studies were performed using same field of view to avoid scaling problems.

In order to match the pixel matrix sizes, CT images were interpolated to 256×256 pixel matrix, SPECT images were expanded to 256×256 pixel matrix, and MR images were left unchanged. Using the contrasting marker points in corresponding cross-sections of the image, cross-sections were identified and displayed side-by-side on the same computer monitor. SPECT images were color coded according to the gray level densities and made transparent.

Phantom Studies

A phantom study was performed to validate the registration process. Correlations among CT, MR, and SPECT were performed on a single well-defined object: an anthropomorphic body phantom containing some organs.

In the phantom study, the liver was defined as the region of interest. The liver and the contrast markers were filled with the necessary contrast material for the different studies. For the CT and MR study a mixture of 150 ml (in 1400 ml water) of iodine based contrast solution and 0.15 gram (in 1400 ml water) $MnCl_2$ was used in the liver, and 20 ml of iodine based contrast solution and 0.05 gram $MnCl_2$ was used in the contrasting marker(s) while for SPECT, Tc-99m with a concentration of 6.66 uCi/cc was used in the liver and 40 uCi/cc in the contrasting marker(s). Since there was not any respiratory or motion artifact with the phantom study, the cast was not manufactured for the phantom. Contrasting markers were attached to the chest region of the phantom covering the liver. Anterior-posterior and posterior-anterior X-ray films were taken to confirm exact positioning of the landmarks before the scan. If the cross-section landmark was not superimposed on the liver, the body of the phantom was repositioned. After having scans with CT, MR and SPECT consecutively, the reconstructed data was transferred by computer for registration.

Patient Studies

The image registration technique was applied to 2 patients. The results are shown here. After informed consent was obtained, a male patient with suspected recurrence of colorectal carcinoma was scheduled for a simulator appointment for fabrication of half-body cast used for immobilization and image registration. Following the cast production and the contrasting marker placement, anterior posterior and posterior-anterior x-ray films were taken to ensure alignment of the markers with the body cast. After that, the patient received approximately 35 mCi of Tc-99m-labeled 88BV59 colorectal human antibody (DeJager et. al., 32 Proc. Am. Assoc. Cancer Res., 184 (1991)). At 4 and 28 hours post-infusion the patient was scanned with a Picker Prism 3 headed SPECT camera. Acquisitions were performed with a single 15% energy window centered at 140 KeV. Forty projections 3 degrees apart for 100 seconds with pixel size 6.25×6.25 mm were acquired into a 64×64 pixel matrix. The contrasting marker system was also in place with 6.66 uCi/cc Tc-99m during the SPECT scan.

A pelvic and a liver scan was performed to cover all suspected colorectal carcinoma areas. Then the patient was transferred to the MRI unit, repositioned on the MRI table and centered to the machine. At the same time $MnCl_2$ contrast material was injected into the marker system. T1 weighted transaxial slices with 10 mm thickness and 2 mm gap and T1 weighted sagittal slices with 5 mm thickness and 2 mm gap were obtained during the data acquisition. MR data transferred to 256×256 pixel matrix. Pixel size was 1.56×1.56 mm. Then both SPECT and MR slices were transferred to the computer. SPECT slices expanded 256×256 pixel matrix.

A female patient was studied prior to resection of a primary colorectal carcinoma with elevated serum CEA. After half-body cast production, the patient was transferred to the CT unit, repositioned on the CT table and centered to the machine. At the same time CT contrast material was injected into the fiducial marker system. A CT scan was obtained from the lungs to the anus after the administration of oral and i.v. contrast. Slices of 10 mm thickness were acquired into a 512×512 matrix with 0.78 mm pixel size. After the CT scan, patient received approximately 10 mCi of I-131-labeled 16.88 IgM antibody. A SPECT scan was performed at 96 hours post infusion with 5.66 μCi/cc Tc-99m in the fiducial system. Acquisitions were performed with dual energy windows yielding two sets of projections: a 15% window centered 140 keV for the fiducial system and 30% window centered 370 keV for the antibody images. Twenty projections for 80 seconds a view over 360° interval were acquired into a 64×64 pixel matrix. Each cross-section was approximately 7.12 mm thick. Pixel size was 6.25×6.25 mm. Both SPECT and CT cross-sections were transferred to the computer. CT and SPECT slices then were interpolated and expanded 256×256 pixel matrix. The SPECT and CT slice pairs were displayed side-by-side on the same monitor. Using the corresponding fiducial marker points slices were identified and registered.

Since axially registered images have two sets of three fiducial marker points (one set for SPECT and one set for CT or MR) the image correlation accuracy has been evaluated by comparing contrasting marker distances (center to center) on the registered scans (FIG. 2). It was 1-2 mm between CT and MR for phantom studies, 3-4 mm between CT or MR and SPECT for transaxial patient images and 6-8 mm between MR and SPECT for sagittal reconstructed images. The accuracy difference between sagittal and transaxial image registration is due to sagittal reconstruction from axial images and fiducial marker position in sagittal images. Also the accuracy difference between transaxial phantom and patient images, registration is performed between CT and MR for phantom studies but it is performed between CT or MR and SPECT for patient images. The low resolution of the SPECT camera affected our registration procedure.

Our experience showed that using markers on the body cast and centering the body cast to the imaging machine with the markers does not provide the maximum achievable accuracy. So, in the possible future studies there are plans to use some skin marks and/or markers in alignment with cast markers. In that case the patient will be centered to the imaging machine not only using the cast marks but also using the skin marks. This will ensure us to the correct alignment of patient and cast.

In our analysis of the Tc-99m-labeled 88BV59 and I-131-labeled 16.88 IgM images, MR-SPECT and CT-SPECT registration suggest certain important applications in which CT-SPECT or MR-SPECT registration may be important. In evaluation of the patient who has undergone surgery in which surgical site may be difficult to evaluate because of scarring, fibrosis, or postoperative inflammatory changes, the determination of recurrence may be difficult to make on MR scan alone. For our male patient image registration using transaxial slices with those MR images and SPECT images at 28 hours post-infusion showed increased uptake in the pre-sacral area and in the uncinate process of the pancreas for antibody agent. Sagittal reconstruction and registration for pre-sacral area also showed increased uptake in the sacral area. For our female patient transaxial registration and sagittal reconstruction and registration of CT and SPECT images at 26 hours post-infusion showed increased uptake of the antibody in the hepatic flexure which corresponds the patient's known primary malignancy.

A method for registration of abdominal antibody images that imposes no requirements on identification of internal anatomical landmarks has been described. The need for identification of landmarks by a user expert in anatomy is unnecessary. Also the method is independent of the non-tumor concentrations of not affected by patient motion. Since reference is not made to an atlas of normal anatomy, patient specific abnormalities are correctly taken into account. Axial studies suing CT, MR, and SPECT may be accurately registered with sagittal or coronal MR and SPECT scans. This technique has important applicability for correlation of anatomic and functional information obtained by CT, MR, and SPECT for clinical and research purposes. For example, colorectal surgeons may correlate anatomical lesions with physiological abnormalities and also accurately correlate structural and functional change following surgical procedures. Colon or liver tumor volumes may be more accurately defined for radiotherapy planning when optimization of tumor dose relative to normal tissue is critical to successful treatment. New possibilities are opened for accurate long-term analysis of the effects of radiation on internal organs using image registration. However, the only expense of this image registration technique besides material cost, is that radiation oncology technicians should be prepared to construct the body case which takes less than 45 minutes. Nuclear and CT technologist using the technique would only need to fill contrast markers with contrasting agent and also place the system on the support means.

It will be understood that the above description of the present invention is susceptible to various modifications, changes and adaptations, and the same are intended to be comprehended within the meaning and range of equivalents of the appended claims.

What is claimed:

1. A method of registering SPECT images with CT or MR images, comprising the steps of:
   (A) aligning and immobilizing a human torso to be imaged on a support means;
   (B) uniquely marking a cross section of the imaged torso by placing at least a portion of said human torso proximate to a contrasting marker means encased in an inert material comprising the support means;
   (C) imaging said human torso using two or more imaging techniques to produce at least two images of said human torso to be imaged; and
   (D) registering said at least two images of said human torso to be imaged to produce a coherent image of said human torso to be imaged.

2. An alignment system for imaging, comprising:
   (A) a support means for alignment and immobilization of a human torso to be imaged; and
   (B) a contrasting marker means, encased in said support means for providing markings which uniquely mark a cross-section of an imaged human torso, the contrasting marker means being encased in an inert material encasement.

3. The alignment system set forth in claim 2 wherein said inert material encasement is selected from the group consisting of solid or foam organic polymer, wood, steel, and ceramic.

4. The alignment system set forth in claim 2, wherein said contrasting marker means is at least one contrasting tube.

5. The alignment system set forth in claim 4, wherein said tube has a pattern approximating the shape of a M.

6. The alignment system set forth in claim 4, wherein said contrasting marker means is at least one tube which can be filled with a contrasting agent.

7. The alignment system set forth in claim 4, wherein said tube has a circular cross-section.

8. The alignment system set forth in claim 4, wherein said tube has a pattern approximating the shape of a N.

9. The alignment system set forth in claim 4, wherein said tube has a pattern approximating the shape of a Z.

10. The alignment system set forth in claim 5, wherein said tube has a pattern approximating the shape of a W.

11. The alignment system set forth in claim 6, wherein said contrasting agent is an iodine based contrast agent.

12. The alignment system set forth in claim 6, wherein said contrasting agent is an iodine based contrast agent.

13. The alignment system set forth in claim 6, wherein said contrasting agent is $MnCl_2$.

14. The alignment system set forth in claim 6, wherein said contrasting agent is 99m-Tc.

15. The alignment system set forth in claim 6, wherein said contrasting agent is 111-In.

16. The alignment system set forth in claim 6, wherein said contrasting agent is 131-I.

17. The alignment system set forth in claim 6, wherein said contrasting agent is 123-I.

* * * * *